United States Patent
Chou

(10) Patent No.: US 11,105,660 B2
(45) Date of Patent: Aug. 31, 2021

(54) WASHABLE PHYSIOLOGICAL STATE SENSING DEVICE

(71) Applicant: SOFT SENSE LIFE TECH PTE. LTD., Singapore (SG)

(72) Inventor: Kuan-Chien Chou, Taipei (TW)

(73) Assignee: SOFT SENSE LIFE TECH PTE. LTD., Singapore (SG)

( * ) Notice: Subject to any disclaimer, the term of this patent is extended or adjusted under 35 U.S.C. 154(b) by 0 days.

(21) Appl. No.: 16/907,414

(22) Filed: Jun. 22, 2020

(65) Prior Publication Data

US 2021/0018345 A1    Jan. 21, 2021

Related U.S. Application Data

(60) Provisional application No. 62/876,092, filed on Jul. 19, 2019.

(51) Int. Cl.
*G01D 11/24*    (2006.01)
*A61B 5/00*    (2006.01)

(52) U.S. Cl.
CPC .......... *G01D 11/245* (2013.01); *A61B 5/6804* (2013.01)

(58) Field of Classification Search
CPC ............................. G01D 11/245; G01D 11/24
See application file for complete search history.

(56) References Cited

U.S. PATENT DOCUMENTS

| | | | |
|---|---|---|---|
| 10,054,496 B2* | 8/2018 | Hong | G01K 13/20 |
| 2013/0041235 A1* | 2/2013 | Rogers | A61B 5/1107 |
| | | | 600/306 |
| 2017/0354372 A1* | 12/2017 | Varadan | A61B 5/25 |
| 2019/0022400 A1* | 1/2019 | Kumar | A61N 1/3987 |
| 2020/0243807 A1* | 7/2020 | Harutyunyan | H01M 10/46 |
| 2020/0249197 A1* | 8/2020 | Chou | H05K 1/0283 |
| 2020/0330002 A1* | 10/2020 | Hsu | A61B 5/1107 |
| 2020/0353239 A1* | 11/2020 | Daniels | A61B 5/296 |

* cited by examiner

*Primary Examiner* — Jamel E Williams
(74) *Attorney, Agent, or Firm* — McClure, Qualey & Rodack, LLP

(57) ABSTRACT

A washable physiological state sensing device, including a flexible carrier, a flexible electrode and a flexible conductive circuit. The flexible carrier is made of elastic material and provided with a bonding surface; The flexible electrode is arranged on the bonding surface, and provided with a flexible substrate and a plurality of conductive particles; The conductive particles are doped in the flexible substrate, and the flexible substrate is made of elastic material. The flexible conductive circuit is arranged on the bonding surface and electrically connected with the flexible electrode.

9 Claims, 4 Drawing Sheets

WASHABLE PHYSIOLOGICAL STATE SENSING DEVICE

CROSS REFERENCE TO RELATED APPLICATIONS

This application claims the benefit of priority of Provisional Application Ser. No. 62/876,092, filed Jul. 19, 2019, the entire contents of which is incorporated herein by reference.

BACKGROUND OF THE INVENTION

Field of the Invention

The present invention relates to an electronic device, in particular, to a washable physiological state sensing device.

Descriptions of the Related Art

As sensing technology becomes more and more mature, the physiological information people obtained through wearable devices can not only be helpful for understanding their physical conditions preliminarily, but also be used as reference for other medical judgments through long-term collecting.

However, it is hard for consumers to accept the application of wearable device on body parts where is close to the armpit, chest, the lower edge of chest or abdomen except for making it into a bracelet, the reason is that most of the sensors on the market now are made of plastic and have a large sensing probe, which will discomfort the users when placed on or contacted to their skin.

In addition, the cleaning of sensor is particularly important due to direct contacting with human skin, but the present sensor is waterproofed through nothing but rubber ring, whereupon the sensor electrode that need to be exposed cannot be effectively washed because it is normally a metal layer made through the process of electroplating or lithography, which will be oxidized easily after washing and also separated from its carrier to fall off. Therefore, it is one of the important subjects to provide a physiological state sensing device that can be washable and suitable for attached to human skin.

SUMMARY OF THE INVENTION

In view of the foregoing, the purpose of this invention is to provide a washable physiological state sensing device, which is water-resistant and suitable for sticking to human skin without discomfort.

To achieve the above, the present invention provides a washable physiological state sensing device, including a flexible carrier, a flexible electrode and a flexible conductive circuit. The flexible carrier is made of elastic material and provided with a bonding surface; The flexible electrode is arranged on the bonding surface, and provided with a flexible substrate and a plurality of conductive particles; The conductive particles are doped in the flexible substrate, and the flexible substrate is made of elastic material. The flexible conductive circuit is arranged on the bonding surface and electrically connected with the flexible electrode.

In one embodiment, the material of flexible carrier is selected from polyurethane (PU), thermoplastic polyurethane (TPU), silicon, rubber, epoxy resin or textile fiber.

In one embodiment, the material of flexible substrate is selected from polyurethane, thermoplastic polyurethane, silicon or rubber.

In one embodiment, the conductive particles include graphene, carbon nano-tube or nano silver.

In one embodiment, the washable physiological state sensing device further includes a flexible cover, which is made of elastic material and covers at least part of the bonding surface of the flexible carrier and the flexible conductive circuit, with part of the flexible electrode exposed.

In one embodiment, the material of the flexible cover is selected from polyurethane, thermoplastic polyurethane, silicon, rubber or UV resistant coating.

In one embodiment, the washable physiological state sensing device further includes an anti-ultraviolet film, which is overlaid on the flexible cover.

In one embodiment, the washable physiological state sensing device further includes an electronic component, which is electrically connected with the flexible conductive circuit.

In one embodiment, the electronic component is selected from a temperature sensor, an acoustic transducer and a combination thereof.

In one embodiment, the electronic component is electrically connected to the flexible electrode.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DESCRIPTION OF THE PREFERRED EMBODIMENT

In the following description, this invention will be explained with reference to embodiments thereof. However, the description of these embodiments is only for purposes of illustration rather than limitation.

Figure 1:
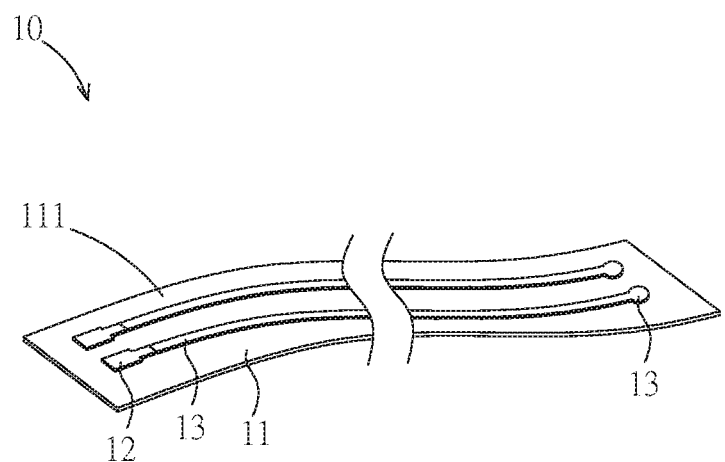
FIG. 1 is a three dimensional view schematic diagram showing a washable physiological state sensing device according to a first embodiment of the invention.
Figure 2:
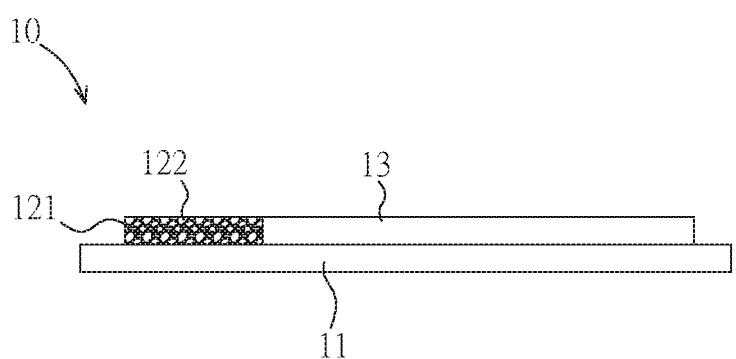
FIG. 2 is a side view schematic diagram showing the washable physiological state sensing device according to the first embodiment of the invention.

Please refer to FIG. 1 and FIG. 2, a washable physiological state sensing device 10 in the first embodiment of the present invention includes a flexible carrier 11, a flexible electrode 12 and a flexible conductive circuit 13.

The flexible carrier 11 is made of elastic material, which is characterized in at least but not limited to flexible, stretchable, twistable or resilient. In the present embodiment, the material of the flexible carrier 11 is selected from polyurethane, thermoplastic polyurethane, silicon, rubber, epoxy resin or textile fiber, wherein the embodiment aspect of epoxy resin can be flexible printed circuit (FPC). In addition, the flexible carrier 11 is also provided with a bonding surface 111.

The flexible electrode 12 is arranged on the bonding surface 111 of the flexible carrier 11 and provided with a flexible substrate 121 and a plurality of conductive particles 122, wherein the conductive particles 122 are doped in the flexible substrate 121. The flexible substrate 121 is made of elastic material that can be selected from but not limited to polyurethane, thermoplastic polyurethane, silicon or rubber. The conductive particles 122 include but not limited to graphene, carbon nano-tube, or nano silver. In other words, the flexible substrate 121 and the conductive particles 122 can be formed by doping in the state of non-solid raw material. It is worth mentioning that the doping concentration of the conductive particle 122 can be adjusted according to the actual demand to achieve the required impedance effect. Moreover, the flexible electrode 12 can be used as the electrode for voltage or current sensing, or as general electrical connection pad to connect with the electrodes of other electronic components.

The flexible conductive circuit 13 is arranged on the bonding surface 111 of the flexible carrier 11 and electrically connected with the flexible electrode 12. In the embodiment, part of the flexible conductive circuit 13 is stretched to partial flexible electrode 12 for a better electrical connection effect, such as increasing the electrical conductivity or reducing the impedance. In other embodiments, it can also be that partial flexible electrode 12 is extended to part of the flexible conductive circuit 13, which can be determined by the process sequence. In addition, the main raw material of the flexible conductive circuit 13 includes graphene, nano silver or carbon nano-tube that can be easily formed by coating or printing.

It is to be noted, the other end opposite to that electrically connected with the flexible electrode 12 can be used as connecting terminal electrically connected with other system circuit boards or control circuit boards. The connection terminal can be zero insertion force (ZIF) type or button attaching type.

In other embodiments, another flexible electrode (not shown in the figure) can be arranged on the other end opposite to that electrically connected with the flexible electrode 12 for more applications. Furthermore, the flexible electrode mentioned can be used as an electric stimulation electrode for the skin or muscle or as an electrode for heating the skin in addition to being used for sensing.

To sum up, the washable physiological state sensing device integrates a flexible substrate with a flexible carrier that characterized in flexible, stretchable, twistable and resilient, and dopes conductive particles into the flexible substrate so that the structure or conductivity of the washable physiological state sensing device will not be damaged after being washed, so the washable physiological state sensing device can be used even though repeatedly cleaned.

Figure 3:
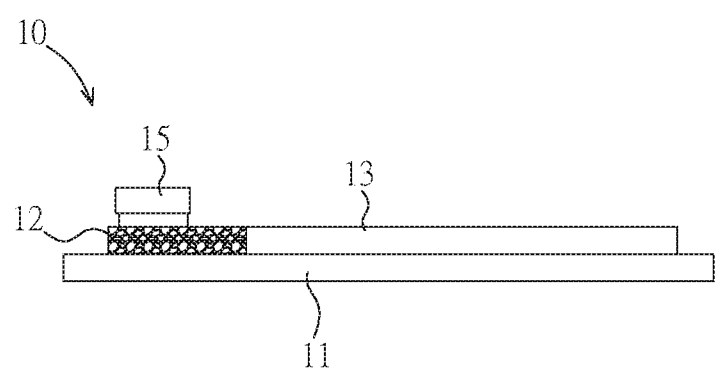
FIG. 3 is the schematic diagrams showing the washable physiological state sensing device according to a first embodiment of the invention.

Moreover, the flexible electrode 12 can be used to connect with other electronic components through medium such as conductive adhesive or conductive bump, as shown in FIG. 3. For example, the electronic component 15 is a micro temperature sensor or an acoustic transducer, the micro temperature sensor can detect the temperature of human body and the acoustic transducer can capture the voice in the chest or abdominal cavity, such as heart sound, breath sound or bowel sound when the washable physiological state sensing device 10 is attached to the skin of the human body, through which the physiological state of the human body can be judged by the back-end computing processor. The aforementioned electronic component 15 may be a MEMS electronic component, such as a MEMS temperature sensor or a MEMS microphone.

Figure 4:
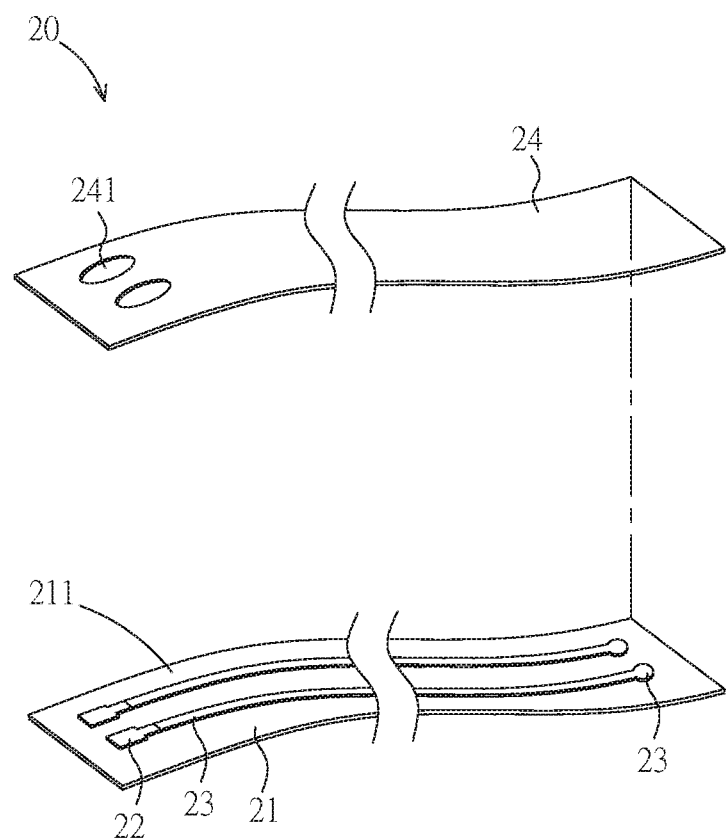
FIG. 4 is a breakdown schematic diagram showing a washable physiological state sensing device according to a second embodiment of the invention.

Referring to FIG. 4, in order to enhance the water resistance, a washable physiological state sensing device 20 in the second embodiment of the present invention includes a flexible carrier 21, a flexible electrode 22, a flexible conductive circuit 23 and a flexible cover 24, wherein the flexible carrier 21, the flexible electrode 22 and the flexible conductive circuit 23 have the same structure and functional characteristics as those in the first embodiment, so it will not be described in detail here.

The flexible cover 24 can be arranged on a bonding surface 211 of the flexible carrier 21 to cover at least part of the flexible conductive circuit 23 and part of the flexible electrode 22. The flexible electrode 22 exposed to an opening 241 of the flexible cover 24 is an electrode to contact the surface under-tested (e.g. skin) or to electrically contact other electronic components. The flexible cover 24 is made of elastic material selected from the polyurethane, thermoplastic polyurethane, silicon, rubber or UV resistant coating.

It is to be noted that the UV resistant coating can also be attached to the flexible cover 24 as a separate UV resistant film (not shown in the figure).

In addition, the combination of the flexible electrode and the flexible carrier mentioned above, as well as the combination of the flexible cover and the flexible carrier, can be bonded by direct hot pressing, or hot melt adhesive, or other adhesives, which is not limited.

Figure 5A:
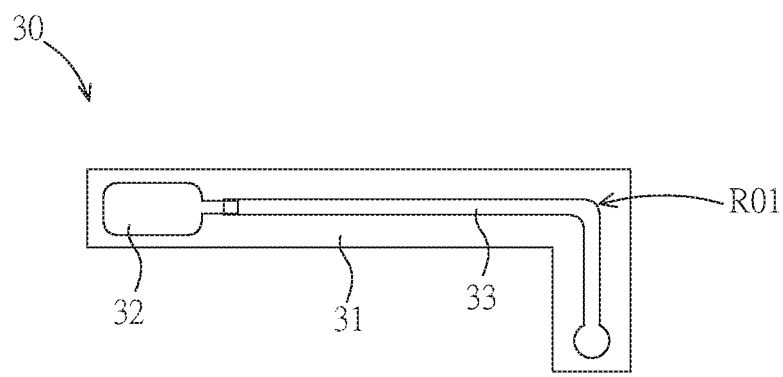
FIG. 5A is a schematic diagram showing an L-shaped washable physiological state sensing device.
Figure 5B:
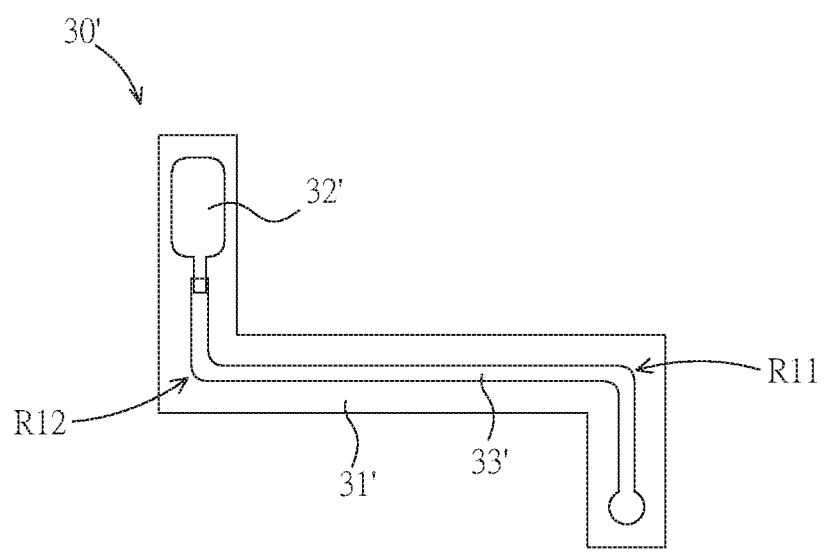
FIG. 5B is a schematic diagram showing an N-shaped washable physiological state sensing device.

The above-mentioned washable physiological state sensing device is based on linear type (or called line shape), while it can also be implemented in different ways such as L-shape, N-shape and S-shape in other embodiments. As shown in FIG. 5A, the washable physiological state sensing device 30 includes a flexible carrier 31, a flexible electrode 32 and a flexible conductive circuit 33. Different from the first embodiment, the washable physiological state sensing device 30 is L-shape, and the flexible conductive circuit 33 is provided with an arc angle or chamfer R01 at the turning point to obtain better electronic conduction property. As shown in FIG. 5B, the washable physiological state sensing device 30' includes a flexible carrier 31', a flexible electrode 32' and a flexible conductive circuit 33', and the washable physiological state sensing device 30' is N-shape as a whole, and the flexible conductive circuit 33' is also provided with an arc angle or chamfer R11 and R12 at the turning point to obtain better electronic conduction property.

The washable physiological state sensing device of the present invention can be directly attached to the skin of human body through the design of different electrode numbers and arrangement modes, or arranged on the textile and then contact the skin of human body for the purpose of sensing or sending signals. The washable physiological state sensing device can be used to obtain the sound of chest or abdominal cavity, such as heart sound, breath sound or bowel sound as well as to measure the temperature, electrocardiography (ECG/EKG), electroencephalography (EEG), electromyography (EMG), the sound of blood flowing in the fistula or body electrical impedance, and also be taken as the electric stimulation electrode for skin or muscle, or the electrode for heating skin.

In conclusion, the washable physiological state sensing device of the present invention is provided with the carrier and the electrode designed with characteristics of flexible, stretchable, twistable or resilient, the conductive particles is doped into the flexible substrate of the flexible electrode and stretchable flexible conductive circuit is used, so the electrode or circuit structure will not be damaged after being washed (including flushed, scrubbed or stirred) and the washable physiological state sensing device can be reused without affecting the measurement characteristics; especially when added with the flexible cover, the overall structure and waterproof washing characteristics of the washable physiological state sensing device can be strengthened and the overall service life can be prolonged.

The above embodiments merely give the detailed technical contents of the present invention and inventive features thereof, and are not to limit the covered range of the present invention. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A washable physiological state sensing device, comprising:
    a flexible carrier, which is made of elastic material and has a bonding surface;
    a flexible electrode, which is arranged on the bonding surface, and has a flexible substrate and a plurality of conductive particles, where the conductive particles are doped in the flexible substrate, and the flexible substrate is made of elastic material;
    a flexible conductive circuit, which is arranged on the bonding surface and electrically connected with the flexible electrode; and
    a flexible cover, which is made of elastic material and covers at least part of the bonding surface of the flexible carrier and the flexible conductive circuit, with part of the flexible electrode exposed.

2. The washable physiological state sensing device of claim 1, wherein the material of flexible carrier is selected from polyurethane (PU), thermoplastic polyurethane (TPU), silicon, rubber, epoxy resin or textile fiber.

3. The washable physiological state sensing device of claim 1, wherein the material of flexible substrate is selected from polyurethane, thermoplastic polyurethane, silicon or rubber.

4. The washable physiological state sensing device of claim 1, wherein the conductive particles include graphene, carbon nano-tube or nano silver.

5. The washable physiological state sensing device of claim 1, wherein the material of the flexible cover is selected from polyurethane, thermoplastic polyurethane, silicon, rubber or UV resistant coating.

6. The washable physiological state sensing device of claim 1, further comprises an anti-ultraviolet film overlaid on the flexible cover.

7. The washable physiological state sensing device of claim 1, further comprises an electronic component electrically connected to the flexible conductive circuit.

8. The washable physiological state sensing device of claim 7, wherein the electronic component is selected from a temperature sensor, an acoustic transducer and a combination thereof.

9. The washable physiological state sensing device of claim 7, wherein the electronic component is electrically connected to the flexible electrode.

* * * * *